US006407277B1

(12) United States Patent
Matsunaga et al.

(10) Patent No.: US 6,407,277 B1
(45) Date of Patent: Jun. 18, 2002

(54) PROCESS FOR THE PREPARATION OF PHOSPHORIC MONOESTER (75) Inventors: Akira Matsunaga; Akira Fujiu; Shinji Tsuyutani, all of Wakayama; Toshio Nozaki, Inba-gun; Masayuki Ueda, Tokyo, all of (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 08/849,211

(22) PCT Filed: Sep. 20, 1995

(86) PCT No.: PCT/JP95/01891
§ 371 (c)(1),
(2), (4) Date: Jun. 9, 1997

(87) PCT Pub. No.: WO96/17852
PCT Pub. Date: Jun. 13, 1996

(30) Foreign Application Priority Data

Dec. 9, 1994 (JP) ............................................. 6-306364

(51) Int. Cl.$^7$ ................................................. C07F 9/09
(52) U.S. Cl. ....................................... 558/110; 558/114
(58) Field of Search .................................. 558/110, 114

(56) References Cited

U.S. PATENT DOCUMENTS

| 4,126,650 A | 11/1978 | Via et al. |
| 4,350,645 A | 9/1982 | Kurosaki et al. |
| 4,670,575 A | 6/1987 | Kurosaki et al. |
| 5,554,781 A | * | 9/1996 | Reierson ..................... 558/110 |

FOREIGN PATENT DOCUMENTS

| GB | A 1 121 683 | 7/1968 |
| JP | 42-6730 | 3/1967 |

OTHER PUBLICATIONS

JP, A, 62 033 190, Patent Abstracts of Japan vol. 11, No. 214 (C–434) Jul. 10, 1987 (Miyoshi Oil & Fat Co. Ltd.) Feb. 13, 1987.

* cited by examiner

Primary Examiner—Joseph K. McKane
Assistant Examiner—Kamal Saeed
(74) Attorney, Agent, or Firm—Oblon, Spivak, McClelland, Maier & Neustadt, P.C.

(57) ABSTRACT

An organic hydroxyl compound is reacted with a phosphorylating agent comprising phosphorus pentaoxide and at least one compound selected from the group consisting of water, phosphoric acid and polyphosphoric acid and having a value represented by formula (I) of from 0.5 to 1.0, under such a condition that the ratio as defined by formula (II) has a value in the range of from 2.8 to 3.2; or alternatively, an organic hydroxyl compound is reacted with the above phosphorylating agent under such a condition that the ratio as defined by formula (II) has a value in the range of from exceeding 3.2 up to 6.4 and then phosphorus pentaoxide is added to the reaction product in such an amount that the ratio as defined by formula (II) has a value in the range of from 2.8 to 3.2 with respect to the total feeds of the starting materials to conduct further reaction. Said process enables the preparation of a phosphoric ester mixture which is excellent in hue and odor, is reduced in the amount of orthophosphoric acid formed as a by-product and contains a phosphoric monoester useful as the component of detergent in an increased amount.

5 Claims, 1 Drawing Sheet

FIG. 1

PROCESS FOR THE PREPARATION OF PHOSPHORIC MONOESTER

This Application is a 371 of PCT/JP 95/01891 filed Sep. 20, 1995.

BACKGROUND OF THE INVENTION

1. Field of the Invention

The present invention relates to a process for the preparation of a phosphoric monoester through the phosphorylation of an organic hydroxyl compound. More particularly, the present invention relates to a process for the preparation of a phosphoric monoester which can easily provide a phosphoric ester mixture having a high phosphoric monoester purity, a reduced orthophosphoric acid content, and good odor and hue.

2. Description of the Related Art

Phosphoric esters of organic hydroxyl compounds are used in a wide field as a detergent, a textile treating agent, an emulsifying agent, a rust preventive, a liquid ion exchanger and a medicament.

Although the reaction of an organic hydroxyl compound with phosphorus pentaoxide has been known as an industrial process for the preparation of a phosphoric ester in the prior art, the product of the reaction comprises mainly a nearly equimolar mixture of a phosphoric monoester represented by the following formula (A) and a phosphoric diester represented by the following general formula (B) (hereinafter, this mixture is referred to as "sesquiphosphate"):

wherein R represents a residue which is obtained by eliminating one hydroxyl group from an organic hydroxyl compound.

There are great differences in properties between a phosphoric monoester and a phosphoric diester. For example, alkali metal salts and alkanolamine salts of phosphoric monoesters of long-chain alkyl alcohols (e.g., lauryl alcohol) are soluble in water, excellent in foaming power and detergency, less toxic and lowly irritant to the skin to be useful as an excellent detergent, while alkali metal salts and alkanolamine salts of phosphoric diesters of long-chain alkyl alcohols are little soluble in water and exhibit foam inhibiting properties rather than little exhibit a foaming power. Therefore, a sesquiphosphate salt containing a large amount of a phosphoric diester salt is unusable as a highly foaming detergent.

Under these circumstances, the development of a process by which a phosphoric ester mixture having a high phosphoric monoester content can be prepared on an industrial scale safely and easily has been eagerly expected and the following processes have been reported to answer this expectation:

(1) a process which comprises reacting an organic hydroxyl compound with phosphorus oxychloride and hydrolyzing the obtained monoalkyl phosphoro-dichloridate;

(2) a process which comprises adding water to an organic hydroxyl compound and thereafter adding phosphorus pentaoxide to the obtained mixture to conduct phosphorylation with the amount of water preliminarily added being 0.5 to 3 mol per mol of phosphorus pentaoxide;

(3) a process which comprises reacting an organic hydroxyl compound with orthophosphoric acid and phosphorus pentaoxide (Japanese Patent Publication-B 42-6730, published on Mar. 18, 1967);

(4) a process which comprises reacting an organic hydroxyl compound with a condensed phosphoric acid (polyphosphoric acid);

(5) a process which comprises reacting an organic hydroxyl compound with a condensed phosphoric acid (polyphosphoric acid) and then recovering, concentrating and reusing excess phosphoric acid;

(6) a process which comprises reacting an organic hydroxyl compound with a phosphorylating agent comprising phosphorus pentaoxide, phosphoric acid and a polyphosphoric acid under such a condition that phosphoric acid components are excess, adding an organic hydroxyl compound to the obtained reaction mixture to make up to a stoichiometric amount and conducting further phosphorylation [see U.S. Pat. No. 4,350,645 (published on Sep. 21, 1982, assignee: Kao Corporation)]; and (7) a process which comprises reacting an organic hydroxyl compound with phosphorus pentaoxide in the presence of water while blowing steam into the reaction system.

However, these processes have respective disadvantages as will now be described, being unsatisfactory as industrial processes for the preparation of phosphoric monoesters.

According to the process (1), three mol of hydrogen chloride is generated in order to prepare one mol of a phosphoric monoester. Accordingly, the process (1) is problematic in the disposal of hydrogen chloride and working atmosphere. Further, according to the process (1), an alkyl chloride is formed as a by-product owing to the presence of hydrogen chloride, so that it is difficult to enhance the phosphoric monoester content of the reaction product.

According to the processes (2) and (3), an organic hydroxyl compound comes into direct contact with highly active phosphorus pentaoxide from the first, though a small amount of water or orthophosphoric acid is present in the reaction system. Therefore, a sesquiphosphate containing a phosphoric diester is formed to lower the purity of the reaction product for a phosphoric monoester. Additionally, these processes have a disadvantage in that the phosphoric monoester formed is decomposed to cause the discoloration of the reaction product and the generation of a nasty odor. When an increased amount of water or orthophosphoric acid is used in order to lower the activity of phosphorus pentaoxide, the orthophosphoric acid content of the product is increased. The contamination of the product with orthophosphoric acid has undesirable influences on some fields, so that the use of the product is limited. For example, when monosodium salt of a phosphoric monoester of a long-chain alkyl alcohol is employed for a paste detergent, disodium phosphate is deposited due to the present of a large amount of orthophosphoric acid. The deposition of disodium phosphate is unfavorable in the use of the detergent.

According to the process (4), a phosphoric monoester can be selectively prepared. However, the amount of orthophosphoric acid formed as a by-product is nearly equal to the reciprocal of the average degree of condensation of the polyphosphoric acid used, so that the contamination of the product with orthophosphoric acid is unavoidable. Accordingly, the process (4) has the same problem as that of the processes (2) and (3). Further, the use of a polyphosphoric acid having an extremely high degree of condensation is necessitated in order to decrease the amount of orthophosphoric acid formed as a by-product according to the process (4). However, in the industrial preparation of such a polyphosphoric acid, the reaction system becomes highly viscous and the materials of the reactor are limited, so that the industrial preparation thereof is extremely difficult.

According to the process (5), a phosphoric monoester can be selectively prepared. Further, the process involves the recovery and reutilization of excess phosphoric acid, being industrially advantageous also in this respect. However, the process uses a large amount of phosphoric acid, so that the recovery thereof necessitates the shouldering of various heavy burdens and the use of considerably complicated equipment. Accordingly, the process cannot easily be conducted.

According to the process (6), the organic hydroxyl compound is added in two portions, so that the obtained reaction product has an enhanced ratio of a phosphoric monoester to a phosphoric diester. However, the reaction system tends to become highly viscous under the condition of an excess of the phosphorylating agent i.e., in the early stages of the reaction to necessitate the use of an industrially special reactor. According to the process (6), additionally, the decomposition of the phosphoric monoester formed proceeds, which lowers the yield of the phosphoric monoester and enhances the orthophosphoric acid content of the reaction product. The increase in the orthophosphoric acid content of the reaction product has undesirable influences on some fields, so that the use of the reaction product is limited.

According to the process (7), the ratio of the phosphoric monoester to the phosphoric diester can be enhanced by blowing steam into the reaction system. However, the blowing of steam into the reaction system increases the amount of orthophosphoric acid formed. Accordingly, the process (7) has the same problem as that of the processes (2), (3) and (4).

As described above, the process using phosphorus oxychloride as a phosphorylating agent is problematic in that hydrogen chloride is generated, while that using a polyphosphoric acid is problematic in that orthophosphoric acid is formed as a by-product and that the materials of the reactor are limited. Among the processes using phosphorus pentaoxide, those involving the direct reaction of an organic hydroxyl compound with phosphorus pentaoxide give a sesquiphosphate containing a phosphoric diester, while that of reacting an organic hydroxyl compound with an excess of a phosphorylating agent in order to lower the phosphoric diester content of the reaction product is problematic in that the reaction system becomes viscous to result in difficult stirring and that a large amount of orthophosphoric acid is formed as a by-product.

The industrial processes for the preparation of phosphoric monoesters according to the prior art have been described above, among which those using phosphorus pentaoxide are advantageous in respect of equipment. Therefore, further improvement in the processes using phosphorus pentaoxide has been expected eagerly.

DISCLOSURE OF THE INVENTION

Summary of the Invention

An object of the present invention is to provide an industrial process for the preparation of a phosphoric monoester according to the phosphorus pentaoxide method which gives a reduced amount of orthophosphoric acid formed as a by-product, can give a phosphoric monoester selectively and in an enhanced yield, and is characterized in that the obtained reaction product is excellent in hue and odor.

Another object of the present invention is to provide an industrial process for the preparation of a phosphoric monoester according to the phosphorus pentaoxide method, by which the phosphorylation can be always conducted in a low-viscosity system.

Under the circumstances described above, the present inventors have made extensive studies on the industrial preparation of a phosphoric monoester. As a result of the studies, they have found that a phosphoric ester mixture which has good hue and odor and an enhanced monoester content and is reduced in the amount of phosphoric acid formed as a by-product can be prepared industrially efficiently by preliminarily mixing the whole or part of the phosphorus pentaoxide to be used in the reaction with at least one compound selected from the group consisting of water, phosphoric acid and a polyphosphoric acid to prepare a phosphorylating agent and adding an organic hydroxyl compound to the phosphorylating agent unlike the feeding order of starting materials according to the prior art. The phosphorylating agent described above takes the form of a heterogeneous system wherein part of the phosphorus pentaoxide fed remains undissolved. The present inventors have also found that an objective phosphoric monoester can be prepared without any increase in the viscosity of the reaction system especially by reacting an organic hydroxyl compound preliminarily with the phosphorylating agent of which the amount is less than the stoichiometric one (i.e., with a phosphorylating agent prepared by using part of the phosphorus pentaoxide to be used in the reaction), and adding the balance of phosphorus pentaoxide to the obtained reaction product to make up to a total amount of ca. stoichiometric one. The present invention has been accomplished on the basis of these findings.

Thus, the present invention provides a process for the preparation of a phosphoric monoester by reacting an organic hydroxyl compound with a phosphorylating agent comprising phosphorus pentaoxide and at least one compound selected from the group consisting of water, phosphoric acid and polyphosphoric acid, under such conditions that a) the ratio as defined by formula (I) has a value in the range of from 0.5 to 1.0, and b) the ratio as defined by formula (II) has a value in the range of from 2.8 to 3.2:

The term "molar amount of organic hydroxyl compound" means the equivalent of hydroxyl group(s) derived from the organic hydroxyl compound.

According to this process, the synthesis of phosphoric esters (phosphorylation) having a high phosphoric monoester purity can be generally achieved substantially only by the above one step.

Further, the present invention provides a process for the preparation of a phosphoric monoester comprising:

(1) a first step of reacting an organic hydroxyl compound with a phosphorylating agent comprising phosphorus pentaoxide and at least one compound selected from the group consisting of water, phosphoric acid and polyphosphoric acid, under such conditions that a) the ratio as defined by formula (I) has a value in the range of from 0.5 to 1.0 and b) the ratio as defined by formula (II) has a value in the range of from exceeding 3.2 up to 6.4, and (2) a second step, wherein phosphorus pentaoxide is added in such an amount that the ratio represented by formula (II) has a value in the range of from 2.8 to 3.2.

According to this process, the synthesis of phosphoric esters (phosphorylation) having a high phosphoric monoester purity can be generally achieved substantially only by the above two steps.

In the formulae (I) and (II), the phosphorylating mixture comprising phosphorus pentaoxide and polyphosphoric acid and/or phosphoric acid (i.e., orthophosphoric acid) and/or water is formally treated as $P_2O_5 \cdot n(H_2O)$ and called as "phosphorylating agent". The molar amount of phosphorylating agent as defined in the formulae (I) and (II) represents the amount (mol) of $P_2O_5$ unit(s) derived from the phosphorylating agent, which is introduced into the reaction system as the starting material. The molar amount of water as defined in the formulae (I) and (II) represents the amount (mol) of water ($H_2O$) derived from the phosphorylating agent, which is introduced into the reaction system as the starting material. The water includes the bound water in the polyphosphoric acid ($P_2O_5 \cdot xH_2O$) and/or orthophosphoric acid ($1/2(P_2O_5 \cdot 3H_2O)$), and free water.

In other words, the present invention relates to a process for the preparation of a phosphoric ester characterized by reacting a phosphorylating agent prepared by mixing phosphorus pentaoxide with water, phosphoric acid or polyphosphoric acid or a mixture of them in such a way that the value represented by the following formula (i):

$$\frac{\left[\begin{array}{c}\text{Molar number of phosphorylating} \\ \text{agent calculated as } P_2O_5\end{array}\right]}{\left[\begin{array}{c}\text{Molar number of water including } nH_2O \\ \text{in the case that phosphorylating} \\ \text{agent is represented by } P_2O_5 \cdot nH_2O\end{array}\right]} \quad (i)$$

will be from 0.5 to 1.0 with an organic hydroxyl compound under such a condition that the value represented by the following formula (ii):

$$\frac{\left[\begin{array}{c}\text{Molar number of water} \\ \text{including } nH_2O \text{ in the case} \\ \text{that phosphorylating} \\ \text{agent is represented by} \\ P_2O_5 \cdot nH_2O\end{array}\right] + \left[\begin{array}{c}\text{Molar number} \\ \text{of organic} \\ \text{hydroxyl} \\ \text{compound}\end{array}\right]}{\left[\begin{array}{c}\text{Molar number of phosphorylating agent} \\ \text{calculated as } P_2O_5\end{array}\right]} \quad (ii)$$

will be from 2.8 to 6.4, and, if necessary, further adding phosphorus pentaoxide thereto in such a way that the value represented by the following formula (iii):

$$\frac{\left[\begin{array}{c}\text{Molar number of water} \\ \text{including } nH_2O \text{ in the} \\ \text{case that the whole} \\ \text{phosphorylating agent is} \\ \text{represented by } P_2O_5 \cdot nH_2O\end{array}\right] + \left[\begin{array}{c}\text{Molar number} \\ \text{of organic} \\ \text{hydroxyl} \\ \text{compound}\end{array}\right]}{\left[\begin{array}{c}\text{Molar number of the whole phosphorylating} \\ \text{agent calculated as } P_2O_5\end{array}\right]} \quad (iii)$$

will be from 2.8 to 3.2 with respect to the total feeds to conduct a reaction.

The phosphorylating agent preferably comprises phosphorus pentaoxide and at least one compound selected from the group consisting of water and phosphoric acid.

The phosphorylating agent may be one prepared by mixing phosphorus pentaoxide with at least one compound selected from the group consisting of water, phosphoric acid and polyphosphoric acid either at 100° C. for up to 4 hours or at 50° C. for up to 10 hours. The phosphorylating agent thus prepared is heterogeneous owing to the presence of phosphorus pentaoxide or its hydrate.

The reaction product obtained by the above process is preferably subjected to hydrolysis and/or deodorization.

The organic hydroxyl compound is desirably a linear or branched, saturated or unsaturated alcohol having 6 to 30 carbon atoms, an adduct of a linear or branched, saturated or unsaturated alcohol having 6 to 30 carbon atoms with 1 or more alkylene oxide(s), wherein the alkylene oxide has 2 to 4 carbon atoms and the number of alkylene oxide molecules added is 1 to 100, or an adduct of an alkylphenol, wherein the alkyl moiety has 6 to 20 carbon atoms, with 1 or more alkylene oxide(s), wherein the alkylene oxide has 2 to 4 carbon atoms and the number of alkylene oxide molecules added is 1 to 100.

Furthermore, the present invention provides a phosphoric monoester obtainable by the process according to the present invention.

The present invention will now be described in detail.

DETAILED DESCRIPTION OF THE INVENTION

The phosphorus pentaoxide in the present invention is a compound also called "phosphoric acid anhydride" and its molecular formula is $P_4O_{10}$ or $P_2O_5$.

The phosphoric acid in the present invention refers to orthophosphoric acid represented by the following formula (C):

(C)

The phosphoric acid is generally available in the market as an aqueous solution of phosphoric acid having a concentration of less than 100% by weight in terms of orthophosphoric acid equivalent (i.e., calculated as $H_3PO_4$). The concentration is not particularly limited, but is preferably 70 to 90% by weight.

The polyphosphoric acid is a condensate of orthophosphoric acid represented by the above formula (C), and has a pyrophosphate bond(s) (P—O—P) in the molecule. The polyphosphoric acid is generally one member selected from the group consisting of linear condensed phosphoric acids represented by formula (F) which will be described below, branched condensed phosphoric acids, cyclic condensed phosphoric acids and cyclic condensed phosphoric acids having a side chain, or a mixture of two or more of them. The polyphosphoric acid may also contain, as one component thereof, orthophosphoric acid represented by the above formula (C). Examples of the linear condensed phosphoric acids include pyrophosphoric acid represented by formula (D) which will be described below and tripolyphosphoric acid represented by formula (E) which will be described below. Examples of the branched condensed phosphoric acids, cyclic condensed phosphoric acids and cyclic condensed phosphoric acids having a side chain include compounds represented by the following formulae (G), (H) and (I) respectively:

Polyphosphoric acid is a phosphoric acid having a concentration of 100% by weight or above in terms of orthophosphoric acid equivalent (i.e., calculated as $H_3PO_4$) and has a homogeneous transparent appearance. The phosphoric acid concentration of the polyphosphoric acid to be used in the present invention is preferably 100 to 120% by weight, though it is not particularly limited.

The organic hydroxyl compound to be used in the present invention is preferably an organic monohydroxyl compound represented by the formula: ROH, though it is not limited thereto as long as it is an organic hydroxyl compound having a hydroxyl group(s). Examples thereof include linear or branched, saturated or unsaturated alcohols having 6 to 30, preferably 8 to 24 carbon atoms, adducts of the alcohols with an alkylene oxide(s) (wherein the alkylene oxide has 2 to 4 carbon atoms and the number of alkylene oxide molecules added is 1 to 100), and adducts of alkylphenols (wherein the alkyl moiety has 6 to 20 carbon atoms) with an alkylene oxide(s) (wherein the alkylene oxide has 2 to 4 carbon atoms and the number of alkylene oxide molecules added is 1 to 100).

Specific examples of the organic hydroxyl compound include octanol, nonyl alcohol, decyl alcohol, undecyl alcohol, lauryl alcohol, myristyl alcohol, pentadecyl alcohol, cetyl alcohol, stearyl alcohol, 2-ethylhexanol, isooctanol, isononanol, isodecanol, isotridecanol and synthetic alcohols such as Oxo alcohol (a product of Nissan Chemical Industry Co. Ltd.), Diadol (a product of Mitsubishi Chemical Co. Ltd.), Dobanol (a product of Mitsubishi Petrochemical Co. Ltd.), Linevol (a product of Showa Shell Chemical Co. Ltd.), Neodol (a product of Shell) and Lial (a product of Eni Chem).

In the present invention, one of these organic hydroxyl compounds or a mixture of two or more of them may be used.

According to the present invention, first, a phosphorylating agent is prepared by mixing phosphorus pentaoxide with at least one compound selected from the group consisting of water, phosphoric acid and polyphosphoric acid in such a way that the ratio as defined by the above formula (I) has a value in the range of from 0.5 to 1.0, preferably from 0.55 to 0.9, still more preferably from 0.60 to 0.85. It is preferable to mix phosphorus pentaoxide with water and/or phosphoric acid, particularly preferably with an aqueous solution of phosphoric acid.

The phosphorylating agent thus prepared contains 0.5 to 1.0 mol of $P_2O_5$ unit per mol of water included in the phosphorylating agent represented as $P_2O_5 \cdot n(H_2O)$. When the value is less than 0.5, the reaction of an organic hydroxyl compound with the resulting phosphorylating agent will give an increased amount of orthophosphoric acid owing to the high water content of the phosphorylating agent. On the contrary, when the value exceeds 1.0, the resulting phosphorylating agent contains highly active phosphorus pentaoxide as such, so that the reaction of an organic hydroxyl compound with the phosphorylating agent will be liable to give sesquiphosphate; and the phosphorylating agent will be viscous to make the operations in the preparations of the phosphorylating agent and the phosphoric monoester difficult.

The order of feeding the starting materials in the preparation of the phosphorylating agent is not particularly limited as far as the final composition satisfies the requirement with respect to the ratio as defined by formula (I). However, it is preferable to add phosphorus pentaoxide gradually to the other material(s) (water, phosphoric acid and/or polyphosphoric acid), because phosphorus pentaoxide generates heat when mixed with water.

The phosphorylating agent according to the present invention may be heterogeneous. In other words, in the present invention, phosphorus pentaoxide may be merely mixed with one compound selected from the group consisting of water, phosphoric acid and polyphosphoric acid. That is, it is not necessitated that they are reacted each other to give a completely homogeneous polyphosphoric acid. In order to prepare a completely homogeneous polyphosphoric acid, the starting material mixture for the phosphorylating agent must be stirred at high temperature or must be aged, and, therefore, another vessel for preparing the phosphorylating agent is necessitated in addition to the reaction vessel in some case.

The phosphorylating agent prepared by mixing phosphorus pentaoxide with at least one compound selected from the group consisting of water, phosphoric acid and polyphosphoric acid can be used as such, i.e., in a heterogeneous state, in the phosphorylation of an organic hydroxyl compound. It is unnecessary to age the phosphorylating agent by heating prior to the use in the phosphorylation. However, the phosphorylating agent may be stirred under heating to suit the convenience of the reaction. The phosphorylating agent cannot be generally converted into a wholly homogeneous polyphosphoric acid even by stirring either at 90° C. for about 5 hours or at 50° C. for about 10 hours. The insoluble matter in this case is believed to be phosphorus pentaoxide hydrate.

In order to attain the effect of the present invention more effectively, it is desirable that the amount of phosphorus pentaoxide to be used in this step is at least 30 mole %, more desirably at least 60 mole %, most desirably at least 70 mole % based on the whole amount of the phosphorylating agent calculated as $P_2O_5$ unit(s).

According to a first embodiment of the present invention, the phosphorylating agent prepared above is reacted with an organic hydroxyl compound under such a condition that the value represented by the above formula (II) ranges from 2.8 to 3.2, which means that phosphorylating agent (calculated as $P_2O_5$ unit(s)) is initially fed in an amount of at least about 0.91 mol per 2 equivalents of hydroxyl groups derived from the organic hydroxyl compound (i.e., in an amount of at least about 91% of the required theoretical amount). When the value represented by the above formula (II) is less than 2.8, which means the presence of an excess of phosphorylating agent, excess phosphorylating agent will be finally converted into orthophosphoric acid, so that the resulting reaction product will contain an increased amount of orthophosphoric acid unfavorably. Further, when the reaction is conducted under such a condition that the ratio as defined by the above formula (II) is less than 2.8, sesquiphosphate is formed with the formation of orthophosphoric acid as a by-product to fail in enhancing the monoester content of the reaction product.

The insolubles contained in the phosphorylating agent according to the present invention may dissolve in the reaction system with the advance of the reaction between the organic hydroxyl compound with the phosphorylating agent.

The phosphorylation under such a condition that the ratio as defined by the above formula (II) ranges from 2.8 to 3.2 is conducted under stirring at generally 30 to 100° C., preferably 50 to 90° C. for generally 0.1 to 10 hours, preferably 0.1 to 8 hours. When the reaction is conducted under the conditions described above, the reaction will be fully attained without the deterioration of the organic hydroxyl compound.

In the present invention, when an organic hydroxyl compound is reacted with the phosphorylating agent under such a condition that the ratio as defined by the above formula (II) ranges from 2.8 to 3.2, the phosphorylation can be generally attained substantially only by this step. In this case, however, the viscosity of the reaction system sometimes increases during the reaction to necessitate the use of a reactor such as kneader suitable for a highly viscous fluid. Therefore, the second embodiment of the present invention which will be described below in detail is more preferable than the first embodiment of the present invention.

According to a second embodiment of the sent invention, the phosphorylating agent is reacted with an organic hydroxyl compound in a first step under such a condition that the ratio as defined by the above formula (II) ranges from higher than 3.2 to 6.4, which means that phosphorylating agent (calculated as $P_2O_5$ unit(s)) is initially fed in an amount of at least 0.37 mol per 2 equivalents of hydroxyl groups derived from the organic hydroxyl compound (i.e., in an amount of at least 37% of the required theoretical amount). When the first step of the reaction is conducted under such a condition that the ratio as defined by the above formula (II) exceeds 6.4, a large amount of unreacted alcohol remains in the reaction system. In this case, the reaction can be advanced by adding phosphorus pentaoxide to the resulting reaction system after the completion of the reaction of the first step. However, a large amount of phosphorus pentaoxide must be added to the reaction system to advance the reaction, which causes increase in the amount of sesquiphosphate formed to lower the purity of the reaction product for the phosphoric monoester unfavorably. The first step is conducted under such a condition that the ratio as defined by the above formula (II) has a value in the range of preferably from 3.5 to 5.5, still more preferably from 4.0 to 5.0.

The insolubles contained in the phosphorylating agent according to the present invention may dissolve in the reaction system with the advance of the reaction between the organic hydroxyl compound with the phosphorylating agent.

The phosphorylation of the first step is conducted under stirring at generally 30 to 100° C., preferably 50 to 90° C. for generally 0.1 to 10 hours, preferably 0.1 to 8 hours. When the reaction is conducted under such conditions, the reaction will be fully attained without the deterioration of the organic hydroxyl compound.

According to the second embodiment of the present invention, after the completion of the reaction of the first step, phosphorus pentaoxide in such an amount that the ratio as defined by the above formula (II) ranges from 2.8 to 3.2 with respect to the total feeds of the starting materials is added to the reaction system to conduct further phosphorylation. That is, when the phosphorylation of an organic hydroxyl compound is conducted under such a condition that the ratio as defined by the above formula (II) ranges from 2.8 to 3.2 (i.e., the first embodiment of the present invention), additional phosphorus pentaoxide need not be added for further phosphorylation, while when the phosphorylation is conducted under such a condition that the ratio as defined by the above formula (II) exceeds 3.2 but is up to 6.4 (i.e., the first step of the second embodiment of the present invention), phosphorus pentaoxide in such an amount that the ratio as defined by the above formula (II) will be in the range of from 2.8 to 3.2 is additionally added to the reaction system to conduct further phosphorylation (the second step of the second embodiment of the present invention).

When the reaction of the second step is conducted under such a condition that the ratio as defined by the above formula (II) exceeds 3.2, the reaction will not be completed to make unreacted organic hydroxyl compound remain in the reaction system, while when it is conducted under such a condition that the ratio is less than 2.8, excess phosphorylating agent will remain in the reaction system finally as orthophosphoric acid. Both of the cases are unfavorable.

The phosphorus pentaoxide for the reaction of the second step may be added by any of batchwise and semibatchwise methods. The latter is preferable to prevent local reaction. The semibatchwise addition may be conducted by a stepwise or continuous method or a combination of both of them.

There may occurs an idea that POCl$_3$, poly-phosphoric acid or a mixture of phosphorus pentaoxide with water is added as the phosphorylating agent for the second stage of the reaction. However, the addition of POCl$_3$ has a disadvantage of generating hydrogen chloride as a by-product, while the use of the other phosphorylating agents has a disadvantage of generating orthophosphoric acid as a by-product. Surprisingly, the addition of phosphorus pentaoxide as it is does not increase the amount of the phosphoric diester formed and can prevent the formation of orthophosphoric acid as a by-product. Further, the addition thereof can enhance the conversion by virtue of the high phosphorylating power of phosphorus pentaoxide.

After the addition of phosphorus pentaoxide, the resulting mixture is subjected to the reaction under stirring at a temperature of generally 40 to 120° C., preferably 60 to 100° C. for generally 1 to 24 hours, preferably 2 to 12 hours. When the reaction is conducted under such conditions, the reaction will effectively advance, and, therefore, the conversion of the organic hydroxyl compound will be sufficiently high and the decomposition of phosphoric esters formed will not be liable to proceed.

Among various embodiments according to the present invention, an embodiment is preferable, which comprises conducting the reaction of the first step under such a condition that the ratio as defined by the above formula (II) exceeds 3.2 but is up to 6.4, preferably be 3.5 to 5, and thereafter adding phosphorus pentaoxide in such an amount that the ratio as defined by the above formula (II) ranges from 2.8 to 3.2, preferably 2.9 to 3.1 to the reaction system to conduct further phosphorylation. According to this embodiment, the phosphorylation can be generally achieved substantially only by the above two steps. When the phosphorylation is conducted according to this embodiment, the viscosity increase of the reaction system can be prevented during the reaction to dispense with an equipment such as an intensive mixer.

Although the reaction product (phosphoric ester mixture) prepared by the above process can be used as such, it is preferable for some uses that the reaction product be subjected to the following post-treatment. Specifically, when a phosphoric ester mixture containing a compound having a pyrophosphate bond such as one represented by the following formula (J) is used in the preparation of toiletries, the resulting toiletries exhibit poor properties:

(J)

wherein X represents a hydrogen atom or a residue obtained by eliminating one hydroxyl group from an organic hydroxyl compound. Therefore, it is preferable that the phosphoric ester mixture be subjected to hydrolysis to cleave the pyrophosphate bond.

The hydrolysis is preferably conducted by adding 1 to 10% by weight (based on the obtained reaction product) of water to the reaction product (phosphoric ester mixture) and keeping the resulting mixture at 60 to 100° C.

The phosphoric ester mixtures each comprising a phosphoric monoester prepared according to the process of the present invention have relatively good odor. In order to result in a further improvement of the odor, especially in cases of phosphoric monoesters each having a long-chain alkyl group, it is preferable that the phosphoric ester mixture be subjected to deodorization. Although the deodorization may be conducted by any of steam distillation, extraction, crystallization and so forth, steam distillation is preferable with that using a thin film being still more preferable.

The phosphoric monoesters prepared by the process of the present invention and salts thereof can be used in a wide field as a detergent, a textile treatment agent, an emulsifying agent, a rust preventive, a liquid ion exchanger, a medicament or the like. The salts of the monoesters includes salts thereof with alkali metals, alkaline earth metals, alkanolamines, basic amino acids and so forth.

For example, in the preparation of a detergent composition containing a phosphoric monoester according to the present invention or a salt thereof, it is preferable that the monoester or salt be used in an amount of 2 to 60% by weight, particularly 10 to 40% by weight based on the whole weight of the composition. In the preparation of the detergent composition, various surfactant which are commonly used in the preparation of detergent compositions may be optionally used in addition to the above phosphoric monoester or the salt.

Examples of the anionic surfactant usable in this case include sulfate, sulfonate and carboxylate type surfactants. Specific examples of the sulfate and sulfonate type surfactants include salts of alkyl sulfates, salts of polyoxyethylene alkyl sulfates; and sulfosuccinate, taurate, isethionate and α-olefin sulfonate type surfactants, while those of the carboxylate type surfactant include fatty acid soaps, ether carboxylate type surfactants and acylated amino acid type surfactants.

Examples of the amphoteric surfactant usable in the above case include carbobetaine type, phosphobetaine type, sulphobetaine type and imidazolinium betaine type surfactants.

Examples of the nonionic surfactant usable therein include polyoxyalkylene addition type, polyoxypropylene-polyoxyethylene addition type, amine oxide type and mono- and di-ethanolamide type surfactants; sorbitan fatty acid esters and adducts thereof with ethylene oxide; glycerol fatty acid esters and adducts thereof with ethylene oxide; sucrose esters and adducts thereof with ethylene oxide; alkylsaccharide type surfactants and adducts thereof with ethylene oxide; and N-polyhydroxy-alkylfatty acid amide type surfactants.

Examples of the cationic surfactant usable therein include quaternary ammonium salts of linear or branched mono- or di-alkyl addition type and adducts thereof wherein alkylene oxide molecules are added to the alkyl group.

These surfactants are each used alone or as a mixture of two or more of them. The amount of the surfactant is preferably 0.1 to 60% by weight, particularly preferably 1 to 50% by weight based on the whole weight of the detergent composition, though the amount varies depending upon the form of the composition.

The detergent composition containing a phosphoric monoester according to the present invention may further contain one or more conventional components for detergent compositions in addition to the above surfactant components so far as the effects of the phosphoric monoester according to the present invention are not impaired. The conventional components include polyhydric alcohols, e.g., ethylene glycol, diethylene glycol, triethylene glycol, polyethylene glycols wherein the degree of polymerization is 4 or above, propylene glycol, dipropylene glycol, polypropylene glycols wherein the degree of polymerization is 3 or above, butylene glycols (such as 1,3-butylene glycol and 1,4-butylene glycol), glycerol, diglycerol, polyglycerols wherein the degree of polymerization is 3 or above, sugar alcohols (such as sorbitol, mannitol, xylitol and maltitol), adducts of glycerols with ethylene oxide (hereinafter abbreviated to "EO") and/or propylene oxide (hereinafter abbreviated at "PO"), adducts of sugar alcohols with EO and/or PO, saccharides (such as galactose, glucose, fructose, sucrose, maltose and lactose) and adducts thereof with EO and/or PO, and glycosides (such as methyl glycoside and ethyl glycoside) and adducts thereof with EO and/or PO; oil components, e.g., hydrocarbons (such as liquid paraffin, squalane, vaseline and solid paraffin), natural fats and oils (such as olive oil, jojoba oil, evening primrose oil, coconut oil and beef tallow), ester oils (such as isopropyl myristate, cetyl isooctanoate and neopentyl glycol dicaprate), silicone oils (such as methyl silicone and methyl phenyl silicone), and higher fatty acids (such as isostearic acid and oleic acid); drugs, e.g., vitamines, antimicrobials (such as triclosan and trichlorocarban), anti-inflammatories (such as dipotassium glycyrrhetinate and tocopherol acetate), anti-dandruff agents (such as zinc pyrithione and Octopirox), activators, refrigerants (such as menthol), and ultraviolet absorbers; water swelling clayey minerals, e.g., montmorillonite, saponite, hectorite, veegum, kunipia, smecton; polymers, e.g., polysaccharides (such as carrageenan, xanthan gum, sodium alginate, pullulan, methyl cellulose, carboxymethyl cellulose, hydroxyethyl cellulose and hydroxypropyl cellulose) and synthetic polymers (such as carboxyvinyl polymer and polyvinyl pyrrolidone); pigments, e.g., inorganic pigments (such as titanium oxide, kaolin, mica, sericite, zinc white and talc) and powdery polymers (such as polymethyl methacrylate and nylon powder); antiseptics, e.g., methyl paraben and butyl paraben; viscosity modifiers, e.g, inorganic salts, polyethylene glycol stearate and ethanol; pearl ingredients; perfumes; dyestuffs; and antioxidants.

The detergent composition can be prepared by a conventional process. Although the detergent composition may take any form selected from among liquid, paste, solid, powder and so forth, it is desirable that the composition takes a liquid or pasty form.

According to the process for the preparation of a phosphoric monoester in the present invention, a phosphoric ester mixture which has an enhanced purity for a monoester and is reduced in the orthophosphoric acid (by-product) content can be prepared extremely easily. Further, the present invention enables the industrial preparation of a phosphoric monoester excellent in odor and hue.

Although the reason why an excellent phosphoric monoester as described above can be prepared by the process of the present invention has not been elucidated as yet, it is presumed to be as follows: the direct reaction of an organic hydroxyl compound with highly active phosphorus pentaoxide gives diester and triester; in the present invention, however, phosphorus pentaoxide is preliminarily reacted with water, so that the activity of phosphorus pentaoxide is controlled to thereby give monoester preferentially. Further, with respect to the qualities, the direct contact of an organic hydroxyl compound or phosphoric esters with highly active phosphorus pentaoxide is prevented in the present invention to therefore give a reaction product excellent in odor and hue.

The liquid detergent composition containing a phosphoric monoester prepared by the process of the present invention does not harm the skin or hair and is excellent in ability to foam and stability, so that it can be used as a detergent component for a product which comes into direct contact with the skin for a long time, for example, kitchen detergent, as well as a shampoo and a body shampoo.

EXAMPLES

The present invention will now be described in more detail by referring to the following Examples and Comparative Examples, though the present invention is not limited to these Examples only.

In the Examples and Comparative Examples, all percentages are by weight, unless otherwise noted.

Example 1

75% phosphoric acid, 19.7 g [$P_2O_5$: 10.7 g (0.075 mol), water: 9.0 g (0.5 mol)], and phosphorus pentaoxide (active ingredient: 98.5%), 37.2 g (0.258 mol), were fed into a reactor (capacity: 1000 ml). The obtained mixture was stirred at 50° C. for 0.5 hour to prepare a heterogeneous phosphorylating agent (the ratio as defined by formula (I): 0.67).

Then, 186.3 g (1.00 mol) of lauryl alcohol (MW: 186.3) was added to the heterogeneous phosphorylating agent at 50° C. and the obtained mixture (the ratio as defined by formula (II): 4.5) was kept at 80° C. for one hour to conduct a reaction. 24.0 g (0.167 mol) of phosphorus pentaoxide (active ingredient: 98.5%) was gradually added to the obtained reaction mixture at 80° C. in 2 hours. After the completion of the addition, the resulting mixture (the ratio as defined by formula (II): 3) was kept at 90° C. for 6 hours to further conduct a reaction. During the above operation, the reaction system was kept at low viscosity, so that no particularly intensive mixer was necessitated.

Then, 13.4 g of deionized water was added to the reaction mixture and the resulting mixture was kept at 90° C. for 2 hours to conduct hydrolysis. The reaction product thus prepared comprised 76.8% of monolauryl phosphate, 13.0% of dilauryl phosphate, 5.9% of orthophosphoric acid and 4.3% of unreacted alcohol, exclusive of water. The hue of the product was 2 by klett.

Further, the reaction product was subjected to deodorization using a steam distillator (heat transfer area: 0.03 m², made of glass) with forced thin film. The steam distillation was conducted at a jacket temperature of 150° C. and 20 mmHg by continuously feeding the reaction product and steam at rates of 100 g/hr and 150 g/hr respectively to give an objective phosphoric monoester-containing product as a residue. The distillate was a mixture comprising unreacted alcohol and water. The residue comprised 80.0% of monolauryl phosphate, 13.6% of dilauryl phosphate, 6.2% of orthophosphoric acid and 0.24% of unreacted alcohol, exclusive of water. The hue klett of the residue was 3 and the odor thereof was good as evaluated organoleptically.

The analysis of the reaction product (or the residue) was conducted as follows:
(Analyses for a Phosphoric Monoester, a Phosphoric Diester and Orthophosphoric acid)

The reaction product was subjected to extraction with diethyl ether to conduct the partition of the product between the ether and water, giving an aqueous phase containing orthophosphoric acid and an organic phase containing a phosphoric monoester and a phosphoric diester. Each phase was subjected to potentiometric titration to determine the orthophosphoric acid content.

More specifically, about 5 g (a g) of a sample, 100 ml of 0.1N hydrochloric acid and 100 ml of diethyl ether were put in a 500-ml separatory funnel. The resulting funnel was vigorously shaken and thereafter allowed to stand, by which the contents were separated into two phases. The lower layer (aqueous phase) was subjected to potentiometric titration with an 0.5N aqueous solution of potassium hydroxide to determine the amount (b mol) of alkali consumed until the reaction reached the first equivalence point and that (c mol) thereof consumed until the reaction reached the second equivalence point. The orthophosphoric acid content was calculated according to the following formula (1):

$$\text{orthophosphoric acid content (wt\%)} = \frac{98.00 \times (c - b)}{a} \times 100. \tag{1}$$

The organic phase was distilled to remove the ether. Tetrahydrofuran was added to the residue to make up to a total amount of 100 ml. 10 ml of the resulting mixture was sampled with a transfer pipette and added to a mixture comprising 55 ml of tetrahydrofuran and 35 ml of deionized water, followed by dissolution. The obtained solution was subjected to potentiometric titration with a 0.5N aqueous solution of potassium hydroxide to determine the amount (d mol) of alkali consumed until the reaction reached the first equivalence point and that (e mol) thereof consumed until the reaction reached the second equivalence point. The phosphoric monoester content and the phosphoric diester content were determined according to the following formulae (2) and (3):

$$\text{phosphoric monoester content (wt\%)} = \frac{e - d}{a} \times \begin{bmatrix} \text{mol. wt. of} \\ \text{phosphoric} \\ \text{monoester} \end{bmatrix} \times 1000 \text{ and} \tag{2}$$

$$\text{phosphoric diester content (wt\%)} = \frac{2d - e}{a} \times \begin{bmatrix} \text{mol. wt. of} \\ \text{phosphoric} \\ \text{diester} \end{bmatrix} \times 1000. \tag{3}$$

(Analysis for Unreacted Organic Hydroxyl Compound)

The analysis for unreacted organic hydroxyl compound was conducted by extraction with petroleum ether. More specifically, 5 to 10 g of a sample was dissolved in a mixture comprising 100 ml of isopropanol and 100 ml of 15% by weight aqueous solution of triethanolamine. The obtained solution was transferred to a 500-ml separatory funnel and extracted with 100 ml of petroleum ether thrice. The petroleum ether phases were combined each other and washed with 100 ml of 50% by volume aqueous solution of ethanol twice and with 100 ml of deionized water once. The resulting petroleum ether phase was dried over anhydrous sodium sulfate and then distilled to remove the petroleum ether. The resulting residue (petroleum ether extract) was dried at room temperature under a reduced pressure (about 200 mmHg) until a constant weight was reached. The weight of the petroleum ether extract was accurately determined.

Further, the hue was determined by the following method.

The reaction product was diluted with a solvent such as ethanol and tetrahydrofuran to 10 w/v %, or the residue was dissolved in such a solvent in a concentration of 10 w/v %. The absorbance of the obtained solution was determined at 420 nm and multiplied by 1000. The obtained value was given as klett. A higher klett means severer yellowing, while a lower klett means nearer colorless. It is preferable that the klett be 15 or below, still more preferably 10 or below.

The odor was evaluated organoleptically.

Comparative Example 1

186.3 g (1.00 mol) of lauryl alcohol (MW: 186.3) and 75% phosphoric acid, 19.7 g [$P_2O_5$: 10.7 g (0.075 mol), water: 9.0 g (0.5 mol)], were fed into a reactor (capacity: 1000 ml). The obtained mixture was stirred at 50° C. for 0.5 hour.

Then, phosphorus pentaoxide (active ingredient: 98.5%), 61.2 g (0.425 mol), was gradually added to the obtained mixture at 50° C. and after the completion of the addition, the resulting mixture was kept at 90° C. for 10 hours to conduct a reaction.

Then, 13.4 g of deionized water was added to the reaction mixture and the resulting mixture was kept at 90° for 2 hours to conduct hydrolysis. The reaction product thus prepared comprised 72.3% of monolauryl phosphate, 16.6% of dilauryl phosphate, 6.8% of orthophosphoric acid and 4.3% of unreacted alcohol, exclusive of water. The hue klett of the product was 20.

Further, the reaction product was subjected to deodorization using a steam distillator with forced thin film. The steam distillation was conducted under the same conditions as those of Example 1. The obtained residue comprised 75.3% of monolauryl phosphate, 17.3% of dilauryl phosphate, 7.1% of orthophosphoric acid and 0.31% of unreacted alcohol, exclusive of water. The hue klett of the residue was 30 and the odor thereof was nasty as evaluated organoleptically.

Example 2

75% phosphoric acid, 15.8 g [($P_2O_5$: 8.59 g (0.061 mol), water: 7.21 g (0.401 mol)], and phosphorus pentaoxide (active ingredient: 98.5%), 39.2 g (0.272 mol), were fed into a reactor (capacity: 1000 ml). The obtained mixture was stirred at 50° C. for 0.5 hour to prepare a heterogeneous phosphorylating agent (the ratio as defined by formula (I): 0.83).

Then, 204.9 g (1.10 mol) of lauryl alcohol (MW: 186.3) was added to the heterogenous phosphorylating agent at 50° C. and the obtained mixture (the ratio as defined by formula (II): 4.5) was kept at 80° C. for one hour to conduct a reaction. 24.0 g (0.167 mol) of phosphorus pentaoxide (active ingredient: 98.5%) was gradually added to the obtained reaction mixture at 80° C. in 2 hours. After the completion of the addition, the resulting mixture (the ratio as defined by formula (II): 3.02) was kept at 90° C. for 6 hours to further conduct a reaction. During the above operation, the reaction system was kept at low viscosity, so that no particularly intensive mixer was necessitated.

Then. 14.2 g of deionized water was added to the reaction mixture and the resulting mixture was kept at 90° C. for 2 hours to conduct hydrolysis. The reaction product thus prepared comprised 76.7% of monolauryl phosphate, 16.1% of dilauryl phosphate, 3.6% of orthophosphoric acid and 3.6% of unreacted alcohol, exclusive of water. The hue klett of the product was 2.

Further, the reaction product was subjected to deodorization using a steam distillator with forced thin film. The steam distillation was conducted under the same conditions as those of Example 1. The obtained residue comprised 79.4% of monolauryl phosphate, 16.7% of dilauryl phosphate, 3.7% of orthophosphoric acid and 0.26% of unreacted alcohol, exclusive of water. The hue klett of the residue was 3 and the odor thereof was good as evaluated organoleptically.

Comparative Example 2

204.9 g (1.10 mol) of lauryl alcohol (MW: 186.3) and 75% phosphoric acid, 15.8 g [$P_2O_5$: 8.58 g (0.060 mol), water: 7.22 g (0.401 mol)], were fed into a reactor (capacity: 1000 ml). The obtained mixture was stirred at 50° C. for 0.5 hour.

Then, phosphorus pentaoxide (active ingredient: 98.5%), 63.4 g (0.44 mol), was gradually added to the obtained mixture at 50° C. and after the completion of the addition, the resulting mixture was kept at 80° C. for 12 hours to conduct a reaction.

Then, 14.2 g of deionized water was added to the reaction mixture and the resulting mixture was kept at 80° C. for 3 hours to conduct hydrolysis. The reaction product thus prepared comprised 72.1% of monolauryl phosphate, 19.9% of dilauryl phosphate, 3.8% of orthophosphoric acid and 4.2% of unreacted alcohol, exclusive of water. The hue klett of the product was 18.

Further, the reaction product was subjected to deodorization using a steam distillator with forced thin film. The steam distillation was conducted under the same conditions as those of Example 1. The obtained residue comprised 75.0% of monolauryl phosphate, 20.7% of dilauryl phosphate, 4.0% of orthophosphoric acid and 0.29% of unreacted alcohol, exclusive of water. The hue klett of the residue was 25 and the odor thereof was nasty as evaluated organoleptically.

Example 3

85% phosphoric acid, 28.2 g [$P_2O_5$: 17.4 g (0.123 mol), water: 10.8 g (0.600 mol)], and phosphorus pentaoxide (active ingredient: 98.5%), 30.3 g (0.210 mol), were fed into a reactor (capacity: 1000 ml). The obtained mixture was stirred at 50° C. for 0.5 hour to prepare a heterogeneous phosphorylating agent (the ratio as defined by formula (I): 0.56).

Then, 167.7 g (0.90 mol) of lauryl alcohol (MW: 186.3) was added to the heterogeneous phosphorylating agent at 50° C. and the obtained mixture (the ratio as defined by formula (II): 4.5) was kept at 80° C. for one hour to conduct a reaction. 24.0 g (0.167 mol) of phosphorus pentaoxide (active ingredient: 98.5%) was gradually added to the obtained reaction mixture at 80° C. in 2 hours. After the completion of the addition, the resulting mixture (the ratio as defined by formula (II): 3) was kept at 90° C. for 6 hours to further conduct a reaction. During the above operation, the reaction system was kept at low viscosity, so that no particularly intensive mixer was necessitated.

Then, 12.5 g of deionized water was added to the reaction mixture and the resulting mixture was kept at 90° C. for 2 hours to conduct hydrolysis. The reaction product thus prepared comprised 79.7% of monolauryl phosphate, 7.2% of dilauryl phosphate, 8.4% of orthophosphoric acid and 4.7% of unreacted alcohol, exclusive of water. The hue klett of the product was 2.

Further, the reaction product was subjected to deodorization using a steam distillator with forced thin film. The steam distillation was conducted under the same conditions as those of Example 1. The obtained residue comprised 83.4% of monolauryl phosphate, 7.5% of dilauryl phosphate, 8.8% of orthophosphoric acid and 0.22% of unreacted alcohol, exclusive of water. The hue klett of the residue was 3 and the odor thereof was good as evaluated organoleptically.

Comparative Example 3

167.7 g (0.9 mol) of lauryl alcohol (MW: 186.3) and 85% phosphoric acid, 28.2 g [$P_2O_5$: 17.4 g (0.123 mol), water: 10.8 g (0.6 mol)], were fed into a reactor (capacity: 1000 ml). The obtained mixture was stirred at 50° C. for 0.5 hour.

Then, phosphorus pentaoxide (active ingredient: 98.5%), 54.3 g (0.377 mol), was gradually added to the obtained mixture at 50° C. and after the completion of the addition, the resulting mixture was kept at 90° C. for 10 hours to conduct a reaction.

Then, 12.5 of deionzed water was added to the reaction mixture and the resulting mixture was kept at 90° C. for 2 hours to conduct hydrolysis. The reaction product thus prepared comprised 75.4% of monolauryl phosphate, 11.7% of dilauryl phosphate, 8.4% of orthophosphoric acid and 4.5% of unreacted alcohol, exclusive of water. The hue klett of the product was 30.

Further, the reaction product was subjected to deodorization using a steam distillator with forced thin film. The steam distillation was conducted under the same conditions as those of Example 1. The obtained residue comprised 78.7% of monolauryl phosphate, 12.2% of dilauryl phosphate, 8.8% of orthophosphoric acid and 0.33% of unreacted alcohol, exclusive of water. The hue klett of the residue was 38 and the odor thereof was nasty as evaluated organoleptically.

Example 4

105% polyphosphoric acid, 37.6 g [($P_2O_5$: 28.6 g (0.202 mol), water: 9.0 g (0.5 mol)], and phosphorus pentaoxide (active ingredient: 98.5%), 18.9 g (0.131 mol), were fed into a reactor (capacity: 1000 ml). The obtained mixture was stirred at 70° C. for 0.5 hour to prepare a heterogeneous phosphorylating agent (the ratio as defined by formula (I): 0.67).

Then, 186.3 g (1.00 mol) of lauryl alcohol (MW: 186.3) was added to the heterogeneous phosphorylating agent at 70° C. and the obtained mixture (the ratio as defined by formula (II): 4.5) was kept at 70° C. for one hour to conduct a reaction. 24.0 g (0.167 mol) of phosphorus pentaoxide (active ingredient: 98.5%) was gradually added to the obtained reaction mixture at 70° C. in 2 hours. After the completion of the addition, the resulting mixture (the ratio as defined by formula (II): 3) was kept at 90° C. for 6 hours to further conduct a reaction. During the above operation, the reaction system was kept at low viscosity, so that no particularly intensive mixer was necessitated.

Then, 26.7 g of deionized water was added to the reaction mixture and the resulting mixture was kept at 80° C. for 3 hours to conduct hydrolysis. The reaction product thus prepared comprised 76.0% of monolauryl phosphate, 13.5% of dilauryl phosphate, 6.1% of orthophosphoric acid and 4.4% of unreacted alcohol, exclusive of water. The hue klett of the product was 3.

Further, the reaction product was subjected to deodorization using a steam distillator with forced thin film. The steam distillation was conducted under the same conditions as those of Example 1. The obtained residue comprised 79.3% of monolauryl phosphate, 14.1% of dilauryl phosphate, 6.4% of orthophosphoric acid and 0.25% of unreacted alcohol, exclusive of water. The hue klett of the residue was 4 and the odor thereof was good as evaluated organoleptically.

Example 5

85% phosphoric acid, 23.5 g [$P_2O_5$: 14.5 g (0.102 mol), water: 9.0 g (0.5 mol)], and phosphorus pentaoxide (active ingredient: 98.5%), 33.3 g (0.234 mol), were fed into a reactor (capacity: 1000 ml). The obtained mixture was stirred at 50° C. for 0.5 hour to prepare a heterogeneous phosphorylating agent (the ratio as defined by formula (I): 0.67).

Then, 172.9 g (1.00 mol) of undecanol (Neodol 1, a product of Shell, MW: 172.9) was added to the heterogeneous phosphorylating agent at 50° C. and the obtained mixture (the ratio as defined by formula (II): 4.46) was kept at 50° C. for 3 hours to conduct a reaction. 24.0 g (0.167 mol) of phosphorus pentaoxide (active ingredient: 98.5%) was gradually added to the obtained reaction mixture at 50° C. in 2 hours. After the completion of the addition, the resulting mixture (the ratio as defined by formula (II): 2.98) was kept at 90° C. for 8 hours to further conduct a reaction. During the above operation, the reaction system was kept at low viscosity, so that no particularly intensive mixer was necessitated.

Then, 12.7 g of deionized water was added to the reaction mixture and the resulting mixture was kept at 90° C. for 3 hours to conduct hydrolysis. The reaction product thus prepared comprised 75.9% of monoundecyl phosphate, 13.6% of diundecyl phosphate, 6.6% of orthophosphoric acid and 3.9% of unreacted alcohol, exclusive of water. The hue klett of the product was 3.

Further, the reaction product was subjected to deodorization using a steam distillator with forced thin film. The steam distillation was conducted under the same conditions as those of Example 1. The obtained residue comprised 78.8% of monoundecyl phosphate, 14.1% of diundecyl phosphate, 6.9% of orthophosphoric acid and 0.20% of unreacted alcohol, exclusive of water. The hue klett of the residue was 4 and the odor thereof was good as evaluated organoleptically.

Example 6

75% phosphoric acid, 19.7 g [$P_2O_5$: 10.7 g (0.075 mol), water: 9.0 g (0.5 mol)], and phosphorus pentaoxide (active ingredient: 98.5%), 37.2 g (0.258 mol), were fed into a reactor (capacity: 1000 ml). The obtained mixture was stirred at 60° C. for 0.5 hour to prepare a heterogeneous phosphorylating agent (the ratio as defined by formula (I): 0.67).

Then, 190.7 g (1.00 mol) of Diadol 115L (a product of Mitsubishi Chemical Co. Ltd., MW: 190.7) was added to the heterogeneous phosphorylating agent at 60° C. and the obtained mixture (the ratio as defined by formula (II): 4.5) was kept at 60° C. for 2 hours to conduct a reaction. 24.0 g (0.167 mol) of phosphorus pentaoxide (active ingredient: 98.5%) was gradually added to the obtained reaction mixture at 60° C. in 2 hours. After the completion of the addition, the resulting mixture (the ratio as defined by formula (II): 3) was kept at 80° C. for 10 hours to further conduct a reaction. During the above operation, the reaction system was kept at low viscosity, so that no particularly intensive mixer was necessitated.

Then, 27.2 g of deionized water was added to the reaction mixture and the resulting mixture was kept at 90° C. for 2 hours to conduct hydrolysis. The reaction product thus prepared comprised 76.0% of monoalkyl phosphate, 13.8% of dialkyl phosphate, 6.1% of orthophosphoric acid and 4.1% of unreacted alcohol, exclusive of water. The hue klett of the product was 2.

Further, the reaction product was subjected to deodorization using a steam distillator with forced thin film. The steam distillation was conducted under the same conditions as those of Example 1. The obtained residue comprised 79.1% of monoalkyl phosphate, 14.4% of dialkyl phosphate, 6.3% of orthophosphoric acid and 0.25% of unreacted alcohol, exclusive of water. The hue klett of the residue was 3 and the odor thereof was good as evaluated organoleptically.

Example 7

85% phosphoric acid, 23.5 g [$P_2O_5$: 14.5 g (0.102 mol), water: 9.0 g (0.5 mol)], and phosphorus pentaoxide (active ingredient: 98.5%), 33.3 g (0.231 mol), were fed into a reactor (capacity: 1000 ml). The obtained mixture was stirred at 50° C. for 1.0 hour to prepare a heterogeneous phosphorylating agent (the ratio as defined by formula (I): 0.67).

Then, 272.5 g (1.00 mol) of stearyl alcohol (MW: 272.5) was added to the heterogeneous phosphorylating agent at 80° C. and the obtained mixture (the ratio as defined by formula (II): 4.5) was kept at 80° C. for 2 hours to conduct a reaction. 24.0 g (0.167 mol) of phosphorus pentaoxide (active ingredient: 98.5%) was gradually added to the obtained reaction mixture at 80° C. in 2 hours. After the completion of the addition, the resulting mixture (the ratio as defined by formula (II): 3) was kept at 100° C. for 3 hours to further conduct a reaction. During the above operation, the reaction system was kept at low viscosity, so that no particularly intensive mixer was necessitated.

Then, 17.7 g of deionized water was added to the reaction mixture and the resulting mixture was kept at 90° C. for 3 hours to conduct hydrolysis. The reaction product thus prepared comprised 76.2% of monostearyl phosphate, 14.6% of distearyl phosphate, 4.7% of orthophosphoric acid and 4.5% of unreacted alcohol, exclusive of water. The hue klett of the product was 3 and the odor thereof was good as evaluated organoleptically.

Comparative Example 4

272.5 g (1.0 mol) of stearyl alcohol (MW: 272.5) and 85% phosphoric acid, 23.5 g [$P_2O_5$: 14.5 g (0.102 mol), water: 9.0 g (0.5 mol)], were fed into a reactor (capacity: 1000 ml). The obtained mixture was stirred at 80° C. for 0.5 hour.

Then, phosphorus pentaoxide (active ingredient: 98.5%), 57.3 g (0.398 mol), was gradually added to the obtained mixture at 80° C. and after the completion of the addition, the resulting mixture was kept at 90° C. for 8 hours to conduct a reaction.

Then, 17.7 g of deionized water was added to the reaction mixture and the resulting mixture was kept at 90° C. for 2 hours to conduct hydrolysis. The reaction product thus obtained comprised 70.8% of monostearyl phosphate, 19.0% of distearyl phosphate, 5.0% of orthophosphoric acid and 5.2% of unreacted alcohol, exclusive of water. The hue klett of the product was 30 and the odor thereof was nasty as evaluated organoleptically.

Example 8

75% phosphoric acid, 19.7 g [$P_2O_5$: 10.7 g (0.075 mol), water: 9.0 g (0.5 mol)], and phosphorus pentaoxide (active ingredient: 98.5%), 61.2 g (0.425 mol), were fed into a reactor (capacity: 1000 ml). The obtained mixture was stirred at 50° C. for 0.5 hour to prepare a heterogeneous phosphorylating agent (the ratio as defined by formula (I): 1).

Then, 186.3 g (1.00 mol) of lauryl alcohol (MW: 186.3) was added to the heterogeneous phosphorylating agent at 50° C. and the obtained mixture (the ratio as defined by formula (II): 3) was kept at 90° C. for 8 hours to conduct a reaction. In the course of the reaction, the reaction system became viscous, so that the system was stirred with an intensive mixer.

Then, 13.4 g of deionized water was added to the reaction mixture and the resulting mixture was kept at 90° C. for 2 hours to conduct hydrolysis. The reaction product thus prepared comprised 77.0% of monolauryl phosphate, 14.1% of dilauryl phosphate, 5.2% of orthophosphoric acid and 3.7% of unreacted alcohol, exclusive of water. The hue klett of the product was 3.

Further, the reaction product was subjected to deodorization using a steam distillator with forced thin film. The steam distillation was conducted under the same conditions as those of Example 1. The obtained residue comprised 79.8% of monolauryl phosphate, 14.6% of dilauryl phosphate, 5.4% of orthophosphoric acid and 0.22% of unreacted alcohol, exclusive of water. The hue klett of the residue was 4 and the odor thereof was good as evaluated organoleptically.

Example 9

85% phosphoric acid, 23.5 g [$P_2O_5$: 14.5 g (0.102 mol), water: 9.0 g (0.5 mol)], and phosphorus pentaoxide (active ingredient: 98.5%), 57.3 g (0.401 mol), were fed into a reactor (capacity: 1000 ml). The obtained mixture was stirred at 50° C. for 0.5 hour to prepare a heterogeneous phosphorylating agent (the ratio as defined by formula (I): 1).

Then 172.9 g (1.00 mol) of undecanol (Neodol 1, a product of Shell, MW: 172.9) was added to the heterogeneous phosphorylating agent at 50° C. and the obtained mixture (the ratio as defined by formula (II): 2.98) was kept at 90° C. for 8 hours to conduct a reaction. In the course of the reaction, the reaction system became viscous, so that the system was stirred with an intensive mixer.

Then, 12.7 g of deionized water was added to the reaction mixture and the resulting mixture was kept at 90° C. for 3 hours to conduct hydrolysis. The reaction product thus prepared comprised 76.2% of monoundecyl phosphate, 14.0% of diundecyl phosphate, 5.8% of orthophosphoric acid and 4.0% of unreacted alcohol, exclusive of water. The hue klett of the product was 3.

Further, the reaction product was subjected to deodorization using a steam distillator with forced thin film. The steam distillation was conducted under the same conditions as those of Example 1. The obtained residue comprised 79.2% of monoundecyl phosphate, 14.6% of diundecyl phosphate, 6.0% of orthophosphoric acid and 0.20% of unreacted alcohol, exclusive of water. The hue klett of the residue was 4 and the odor of the residue was good as evaluated organoleptically.

The results of Examples 1 to 9 and Comparative Examples 1 to 4 are given in Table 1, wherein the purity for phosphoric monoester, orthophosphoric acid (as a by-product) rate, hue and odor of the reaction product and the conversion of the starting organic hydroxyl compound are described. Further, FIG. 1 shows the relationships between purity for a phosphoric monoester and orthophosphoric acid (as a by-product) rate with respect to the reaction products which are prepared in Examples 1 to 3 and Comparative Examples 1 to 3, respectively.

Figure 1:
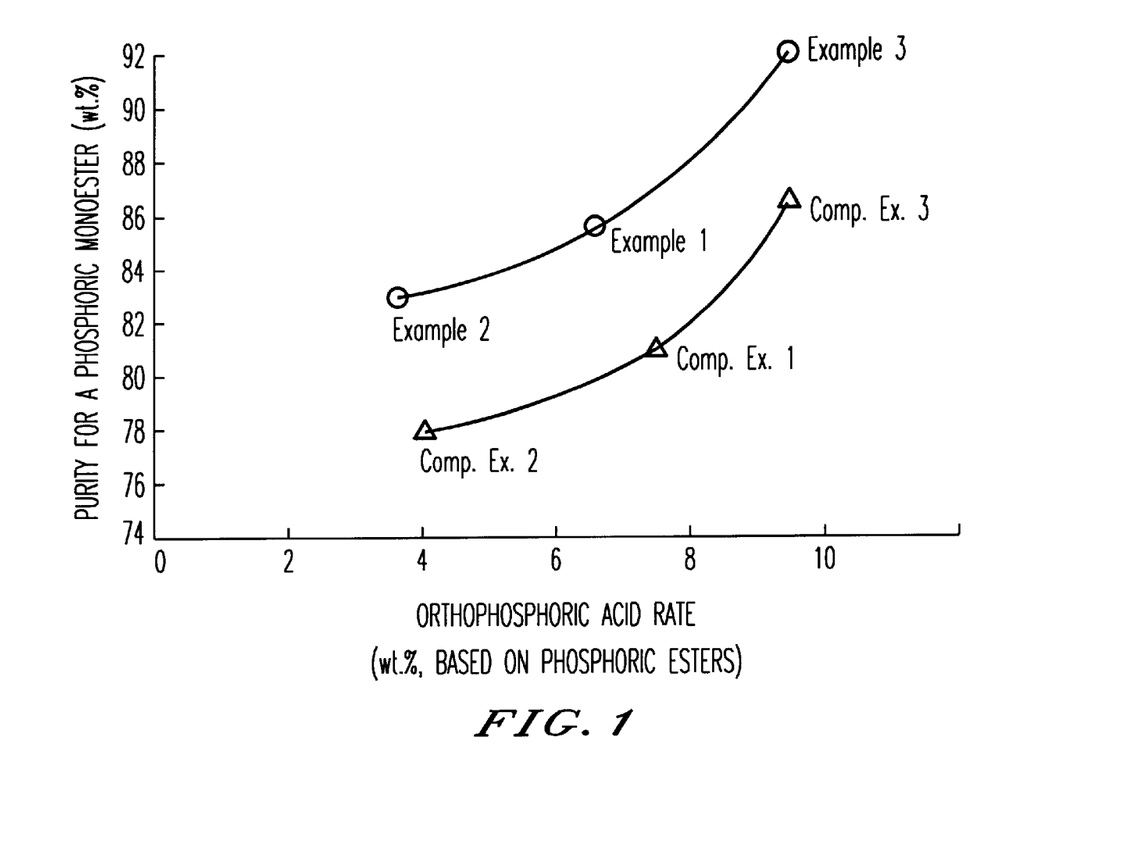
FIG. 1 is a graph showing the relationships between purity for a phosphoric monoester and orthophosphoric acid (as a by-product) rate with respect to the reaction products which are prepared in Examples 1 to 3 and Comparative Examples 1 to 3, respectively.

As apparent from the results of Table 1 and FIG. 1, the phosphorylation of an organic hydroxyl compound with phosphorus pentaoxide in the presence of water is characterized in that as the ratio of water to an organic hydroxyl compound increases, the purity for a phosphoric monoester of the product increases with increase in the orthophosphoric acid rate of the product. When an Example product is compared with a Comparative product, the purity of the Example product for a phosphoric monoester is higher than that of Comparative product for a phosphoric monoester, when the orthophosphoric acid rates of both products are the same, while the orthophosphoric acid rate of the Example product is lower than that of the Comparative product, when the purities of both products for phosphoric monoesters are the same. Further, the products of Examples 1 to 9 are also excellent in hue. Furthermore, the above results revealed that the products of Examples 1 to 9, including both deodorized and undeodorized ones, are superior to those of Comparative Examples in odor.

Accordingly, it can be understood that the process of the present invention enables the preparation of a phosphoric ester mixture which has an enhanced purity for a phosphoric monoester, is reduced in the orthophosphoric acid (as a by-product) rate and exhibits good odor and hue.

TABLE 1

| | Kind of organic hydroxyl compound | Ratio of total feeds of starting materials organic hydroxyl compound/water/$P_2O_5$ (molar ratio) | Purity for a phosphoric monoester[1] (wt %) | Orthophosphoric acid rate[2] (wt %) | Hue[3] klett | Odor after deodorization | Conversion[5] |
|---|---|---|---|---|---|---|---|
| Ex. 1 | lauryl alcohol | 2.0/1.0/1 | 85.5 | 6.57 | 2 | good | 93.8 |
| Comp. Ex. 1 | lauryl alcohol | 2.0/1.0/1 | 81.3 | 7.65 | 20 | nasty | 93.8 |
| Ex. 2 | lauryl alcohol | 2.2/0.8/1 | 82.7 | 3.88 | 2 | good | 95.0 |
| Comp. Ex. 2 | lauryl alcohol | 2.2/0.8/1 | 78.4 | 4.13 | 18 | nasty | 94.0 |
| Ex. 3 | lauryl alcohol | 1.8/1.2/1 | 91.7 | 9.67 | 2 | good | 93.0 |
| Comp. Ex. 3 | lauryl alcohol | 1.8/1.2/1 | 86.6 | 9.64 | 30 | nasty | 93.3 |
| Ex. 7 | stearyl alcohol | 2.0/1.0/1 | 83.9 | 5.18 | 3 | good[4] | 94.0 |

TABLE 1-continued

| | Kind of organic hydroxyl compound | Ratio of total feeds of starting materials organic hydroxyl compound/water/P$_2$O$_5$ (molar ratio) | Purity for a phosphoric monoester*[1] (wt %) | Orthophosphoric acid rate*[2] (wt %) | Hue*[3] klett | Odor after deodorization | Conversion*[5] |
|---|---|---|---|---|---|---|---|
| Comp. Ex. 4 | stearyl alcohol | 2.0/1.0/1 | 78.8 | 5.57 | 30 | nasty*[4] | 93.3 |
| Ex. 4 | lauryl alcohol | 2.0/1.0/1 | 84.9 | 6.82 | 3 | good | 93.5 |
| Ex. 5 | Neodol 1 | 2.0/1.0/1 | 84.8 | 7.37 | 3 | good | 94.1 |
| Ex. 6 | Diadol 115L | 2.0/1.0/1 | 84.6 | 6.79 | 2 | good | 94.2 |
| Ex. 8 | lauryl alcohol | 2.0/1.0/1 | 84.5 | 5.71 | 3 | good | 94.6 |
| Ex. 9 | Neodol 1 | 2.0/1.0/1 | 84.5 | 6.43 | 3 | good | 94.1 | notes)
*[1] the purity of the reaction product (before deodorization) for a phosphoric monoester as calculated according to the following formula:

$$\frac{\text{phosphoric monoester content (wt \%)}}{\text{phosphoric monoester content (wt \%)} + \text{phosphoric diester content (wt \%)}} \times 100$$

*[2] the orthophosphoric acid rate of the reaction product (before deodorization) as calculated according to the following formula:

$$\frac{\text{orthophosphoric acid content (wt \%)}}{\text{phosphoric monoester content (wt \%)} + \text{phosphoric diester content (wt \%)}} \times 100$$

*[3] the hue of the reaction product (before deodorization)
*[4] the odor of the reaction product (before deodorization)
*[5] the conversion of an organic hydroxyl compound as calculated according to the following formula:

$$\left[1 - \frac{\text{organic hydroxyl compound content (wt \%)}}{\frac{[\text{phosphoric monoester content (wt \%)}] \times [\text{MW of unreacted organic compound}]}{\text{MW of phosphoric monoester}} + \frac{[\text{phosphoric diester content (wt \%)}] \times [\text{MW of unreacted organic compound}] \times 2}{\text{MW of phosphoric diester}} + [\text{unreacted organic hydroxyl compound content (wt \%)}]}\right] \times 100$$

Comparative Examples will now be described to explain why the mixing ratio of starting materials is limited in the present invention.

Comparative Example 5

75% phosphoric acid, 19.7 g [P$_2$O$_5$: 10.7 g (0.075 mol), water: 9.0 g (0.5 mol)], and 18.0 g (0.125 mol) of phosphorus pentaoxide (active ingredient: 98.5%) were fed into a reactor (capacity: 1000 ml). The obtained mixture was stirred at 50° C. for 0.5 hour to prepare a heterogeneous phosphorylating agent (the ratio as defined by formula (I): 0.4).

Then, 186.3 g (1.00 mol) of lauryl alcohol (MW: 186.3) was added to the heterogeneous phosphorylating agent at 50° C. and the obtained mixture (the ratio as defined by formula (II): 7.5) was kept at 80° C. for one hour to conduct a reaction. Phosphorus pentaoxide (active ingredient: 98.5%), 43.2 g (0.3 mol), was gradually added to the obtained reaction mixture at 80° C. in 2 hours. After the completion of the addition, the resulting mixture (the ratio as defined by formula (II): 3) was kept at 90° C. for 6 hours to further conduct a reaction.

Then, 13.4 g of deionized water was added to the obtained reaction mixture and the resulting mixture was kept at 90° C. for 2 hours to conduct hydrolysis. The reaction product thus prepared comprised 72.0% of monolauryl phosphate, 16.2% of dilauryl phosphate, 6.6% of orthophosphoric acid and 5.2% of unreacted alcohol, exclusive of water. The hue klett of the product was 13.

Further, the reaction product was subjected to deodorization using a steam distillator with forced thin film. The steam distillation was conducted under the same conditions as those of Example 1. The obtained residue comprised 75.6% of monolauryl phosphate, 17.0% of dilauryl phosphate, 6.9% of orthophosphoric acid and 0.5% of unreacted alcohol, exclusive of water. The hue klett of the residue was 15 and the odor thereof was nasty as evaluated organoleptically.

Comparative Example 6

75% phosphoric acid, 19.7 g [P$_2$O$_5$: 10.7 g (0.075 mol), water: 9.0 g (0.5 mol)], and 18.0 g (0.125 mol) of phosphorus pentaoxide (active ingredient: 98.5%) were fed into a reactor (capacity: 1000 ml). The obtained mixture was stirred at 50° C. for 0.5 hour to prepare a heterogeneous phosphorylating agent (the ratio as defined by formula (I): 0.4).

Then, 74.5 g (0.4 mol) of lauryl alcohol (MW: 186.3) was added to the heterogeneous phosphorylating agent at 50° C. and the obtained mixture (the ratio as defined by formula (II): 4.5) was kept at 80° C. for one hour to conduct a reaction. Phosphorus pentaoxide (active ingredient: 98.5%), 14.4 g (0.1 mol), was gradually added to the obtained reaction mixture at 80° C. in 2 hours. After the completion of the addition, the resulting mixture (the ratio as defined by formula (II): 3) was kept at 90° C. for 6 hours to further conduct a reaction.

Then, 6.3 g of deionized water was added to the obtained reaction mixture and the resulting mixture was kept at 90° C. for 2 hours to conduct hydrolysis. The reaction product thus prepared comprised 67.3% of monolauryl phosphate, 6.1% of dilauryl phosphate, 20.3% of orthophosphoric acid and 6.3% of unreacted alcohol, exclusive of water. The hue klett of the product was 12.

Further, the reaction product was subjected to deodorization using a steam distillator with forced thin film. The steam distillation was conducted under the same conditions as those of Example 1. The obtained residue comprised 71.5% of monolauryl phosphate, 6.5% of dilauryl phosphate, 21.6% of orthophosphoric acid and 0.4% of unreacted alcohol, exclusive of water. The hue klett of the residue was 14 and the odor thereof was nasty as evaluated organoleptically.

Comparative Example 7

In order to prepare a phosphorylating agent wherein the ratio as defined by formula (I) is 1.2, 75% phosphoric acid, 19.7 g [$P_2O_5$: 10.7 g (0.075 mol), water: 9.0 g (0.5 mol)], and 75.7 g (0.525 mol) of phosphorus pentaoxide (active ingredient: 98.5%) were fed into a reactor (capacity: 1000 ml) and the obtained mixture was stirred. The system turned into glassy solid, which could not be stirred.

Comparative Example 8

75% phosphoric acid, 19.7 g [$P_2O_5$: 10.7 g (0.075 mol), water; 9.0 g (0.5 mol)], and 37.2 g (0.258 mol) of phosphorus pentaoxide (active ingredient: 98.5%) were fed into a reactor (capacity: 1000 ml). The obtained mixture was stirred at 50° C. for 0.5 hour to prepare a heterogeneous phosphorylating agent (the ratio as defined by formula (I): 0.67).

Then, 62.0 g (0.333 mol) of lauryl alcohol (MW: 186.3) was added to the heterogeneous phosphorylating agent at 50° C. and the obtained mixture (the ratio as defined by formula (II): 2.5) was kept at 80° C. for one hour to conduct a reaction. 30.9 g (0.166 mol) of lauryl alcohol (MW: 186.3) was added to the obtained reaction mixture and after the completion of the addition, the resulting mixture (the ratio as defined by formula (II): 3) was kept at 90° C. for 6 hours to further conduct a reaction.

Then, 7.5 g of deionized water was added to the obtained reaction mixture and the resulting mixture was kept at 90° C. for 2 hours to conduct hydrolysis. The reaction product thus prepared comprised 68.4% of monolauryl phosphate, 7.6% of dilauryl phosphate, 16.8% of orthophosphoric acid and 7.2% of unreacted alcohol, exclusive of water. The hue klett of the product was 14.

Further, the reaction product was subjected to deodorization using a steam distillator with forced thin film. The steam distillation was conducted under the same conditions as those of Example 1. The obtained residue comprised 73.2% of monolauryl phosphate, 8.2% of dilauryl phosphate, 18.0% of orthophosphoric acid and 0.6% of unreacted alcohol, exclusive of water. The hue klett of the residue was 18 and the odor thereof was nasty as evaluated organoleptically.

Comparative Example 9

75% phosphoric acid, 19.7 g [($P_2O_5$: 10.7 g (0.075 mol), water: 9.0 g (0.5 mol)], and 37.2 g (0.258 mol) of phosphorus pentaoxide (active ingredient: 98.5%) were fed into a reactor (capacity: 1000 ml). The obtained mixture was stirred at 50° C. for 0.5 hour to prepare a heterogeneous phosphorylating agent (the ratio as defined by formula (I): 0.67).

Then, 341.1 g (1.83 mol) of lauryl alcohol (MW: 186.3) was added to the heterogeneous phosphorylating agent at 50° C. and the obtained mixture (the ratio as defined by formula (II): 7.0) was kept at 80° C. for one hour to conduct a reaction. 64.0 g (0.444 mol) of phosphorus pentaoxide (active ingredient: 98.5%) was gradually added to the obtained reaction mixture at 80° C. in 2 hours and after the completion of the addition, the resulting mixture (the ratio as defined by formula (II): 3) was kept at 90° C. for 6 hours to further conduct a reaction.

Then, 23.1 g of deionized water was added to the obtained reaction mixture and the resulting mixture was kept at 90° C. for 2 hours to conduct hydrolysis. The reaction product thus prepared comprised 62.1% of monolauryl phosphate, 29.2% of dilauryl phosphate, 3.3% of orthophosphoric acid and 5.4% of unreacted alcohol, exclusive of water. The hue klett of the product was 18.

Further, the reaction product was subjected to deodorization using a steam distillator with forced thin film. The steam distillation was conducted under the same conditions as those of Example 1. The obtained residue comprised 65.0% of monolauryl phosphate, 30.5% of dilauryl phosphate, 3.5% of orthophosphoric acid and 1.0% of unreacted alcohol, exclusive of water. The hue klett of the residue was 20 and the odor thereof was nasty as evaluated organoleptically.

Comparative Example 10

75% phosphoric acid, 19.7 g [$P_2O_5$: 10.7 g (0.075 mol), water: 9.0 g (0.5 mol)], and 37.2 g (0.258 mol) of phosphorus pentaoxide (active ingredient: 98.5%) were fed into a reactor (capacity: 1000 ml). The obtained mixture was stirred at 50° C. for 0.5 hour to prepare a heterogeneous phosphorylating agent (the ratio as defined by formula (I): 0.67).

Then, 186.3 g (1.0 mol) of lauryl alcohol (MW: 186.3) was added to the heterogeneous phosphorylating agent at 50° C. and the obtained mixture (the ratio as defined by formula (II): 4.5) was kept at 80° C. for one hour to conduct a reaction. 17.6 g (0.122 mol) of phosphorus pentaoxide (active ingredient: 98.5%) was gradually added to the obtained reaction mixture at 80° C. in 2 hours and after the completion of the addition, the resulting mixture (the ratio as defined by formula (II): 3.3) was kept at 90° C. for 6 hours to further conduct a reaction.

Then, 13.0 g of deionized water was added to the obtained reaction mixture and the resulting mixture was kept at 90° C. for 2 hours to conduct hydrolysis. The reaction product thus prepared comprised 66.3% of monolauryl phosphate, 16.8% of dilauryl phosphate, 6.1% of orthophosphoric acid and 10.8% of unreacted alcohol, exclusive of water. The hue klett of the product was 15.

Further, the reaction product was subjected to deodorization using a steam distillator with forced thin film. The steam distillation was conducted under the same conditions as those of Example 1. The obtained residue comprised 73.7% of monolauryl phosphate, 18.7% of dilauryl phosphate, 6.8% of orthophosphoric acid and 0.8% of unreacted alcohol, exclusive of water. The hue klett of the residue was 19 and the odor thereof was nasty as evaluated organoleptically.

Comparative Example 11

75% phosphoric acid, 19.7 g [$P_2O_5$: 10.7 g (0.075 mol), water: 9.0 g (0.5 mol)], and 37.2 g (0.258 mol) of phosphorus pentaoxide (active ingredient: 98.5%) were fed into a reactor (capacity: 1000 ml). The obtained mixture was stirred at 50° C. for 0.5 hour to prepare a heterogeneous phosphorylating agent (the ratio as defined by formula (I): 0.67).

Then, 186.3 g (1.0 mol) of lauryl alcohol (MW: 186.3) was added to the heterogeneous phosphorylating agent at 50° C. and the obtained mixture (the ratio as defined by formula (II): 4.5) was kept at 80° C. for one hour to conduct a reaction. 38.5 g (0.267 mol) of phosphorus pentaoxide (active ingredient: 98.5%) was gradually added to the obtained reaction mixture at 80° C. in 2 hours and after the completion of the addition, the resulting mixture (the ratio as defined by formula (II): 2.5) was kept at 90° C. for 6 hours to further conduct a reaction.

Then, 14.1 g of deionized water was added to the obtained reaction mixture and the resulting mixture was kept at 90° C. for 2 hours to conduct hydrolysis. The reaction product thus prepared comprised 65.9% of monolauryl phosphate, 16.6% of dilauryl phosphate, 12.9% of orthophosphoric acid and 4.6% of unreacted alcohol, exclusive of water. The hue klett of the product was 15.

Further, the reaction product was subjected to deodorization using a steam distillator with forced thin film. The steam distillation was conducted under the same conditions as those of Example 1. The obtained residue comprised 68.7% of monolauryl phosphate, 17.3% of dilauryl phosphate, 13.5% of orthophosphoric acid and 0.5% of unreacted alcohol, exclusive of water. The hue klett of the residue was 18 and the odor thereof was nasty as evaluated organoleptically.

56.2 g [$P_2O_5$: 47.2 g (0.333 mol), water: 9.0 g (0.5 mol)], was added to the obtained reaction mixture at 80° C. and the resulting mixture (the ratio as defined by formula (II): 3) was kept at 90° C. for 6 hours to further conduct a reaction.

Then, 15.0 g of deionized water was added to the obtained reaction mixture and the resulting mixture was kept at 90° C. for 2 hours to conduct hydrolysis. The reaction product thus prepared comprised 67.5% of monolauryl phosphate, 6.7% of dilauryl phosphate, 17.3% of orthophosphoric acid and 8.5% of unreacted alcohol, exclusive of water. The hue klett of the product was 7.

Further, the reaction product was subjected to deodorization using a steam distillator with forced thin film. The steam distillation was conducted under the same conditions as those of Example 1. The obtained residue comprised 73.4% of monolauryl phosphate, 7.3% of dilauryl phosphate, 18.8% of orthophosphoric acid and 0.5% of unreacted alcohol, exclusive of water. The hue klett of the residue was 10 and the odor thereof was nasty as evaluated organoleptically.

The results of Comparative Examples 5 to 12 are given in Table 2, wherein the purity for a phosphoric monoester, orthophosphoric acid (as a by-product) rate, hue and odor of the product and the conversion of the starting organic hydroxyl compound are described.

The notes *1 to *3 and *5 in Table 2 are the same as those in Table 1.

TABLE 2

| | Kind of org. hydroxyl compound | Ratio of total feeds of starting materials organic hydroxyl compound/water/$P_2O_5$ (molar ratio) | Purity for a phosphoric monoester[#1] (wt %) | Orthophosphoric acid rate[#2] (wt %) | Hue[#3] klett | Odor after deodorization | Conversion[#5] (%) |
|---|---|---|---|---|---|---|---|
| Comp. Ex. 5 | lauryl alcohol | 2.0/1.0/1 | 81.6 | 7.5 | 13 | nasty | 92.5 |
| Comp. Ex. 6 | lauryl alcohol | 2.0/2.5/1.5 | 91.7 | 27.7 | 14 | nasty | 89.2 |
| Comp. Ex. 8 | lauryl alcohol | 1.5/1.5/1.0 | 90.0 | 22.1 | 14 | nasty | 88.2 |
| Comp. Ex. 9 | lauryl alcohol | 3.7/1.0/1.6 | 68.0 | 3.6 | 18 | nasty | 92.7 |
| Comp. Ex. 10 | lauryl alcohol | 2.0/1.0/0.9 | 79.8 | 7.3 | 15 | nasty | 84.9 |
| Comp. Ex. 11 | lauryl alcohol | 2.0/1.0/1.2 | 79.9 | 15.6 | 15 | nasty | 92.8 |
| Comp. Ex. 12 | lauryl alcohol | 1.5/1.5/1.0 | 91.0 | 23.3 | 7 | nasty | 86.0 |

Comparative Example 12

75% phosphoric acid, 19.7 g [$P_2O_5$: 10.7 g (0.075 mol), water: 9.0 g (0.5 mol)], and 37.2 g (0.258 mol) of phosphorus pentaoxide (active ingredient: 98.5%) were fed into a reactor (capacity: 1000 ml). The obtained mixture was stirred at 50° C. for 0.5 hour to prepare a heterogeneous phosphorylating agent (the ratio as defined by formula (I): 0.67).

Then, 186.3 g (1.0 mol) of lauryl alcohol (MW: 186.3) was added to the heterogeneous phosphorylating agent at 50° C. and the obtained mixture (the ratio as defined by formula (II): 4.5) was kept at 80° C. for one hour to conduct a reaction. 116% (calculated as $P_2O_5$) polyphosphoric acid, There will now be described Formulation Examples with respect to the detergent composition using the phosphoric monoester prepared in the above Example.

Formulation Example 1

(Shampoo)

| (1) | sodium lauryl ether sulfate | 12% |
|---|---|---|
| (2) | coconut oil fatty acid diethanolamide | 3% |
| (3) | Na salt of the phosphoric monoester prepared in Example 1 | 10% |

-continued

| | | |
|---|---|---|
| (4) | cationized cellulose | 0.2% |
| (5) | fragrance | 0.5% |
| (6) | water | the balance |

According to the above formulation, the above components (1) to (4) were added to hot water (6) to conduct dissolution. The obtained solution was cooled, followed by the addition of the above component (5). A transparent shampoo was prepared. When the hair was washed with this shampoo, the shampoo was lowly irritant, exhibited a high ability to foam and was excellent in feelings in use.

Formulation Example 2
(Body Shampoo)

| | | |
|---|---|---|
| (1) | Na salt of the phosphoric monoester prepared in Example 1 | 15% |
| (2) | lauroylamidopropyldimethylacarboxy-betaine | 3% |
| (3) | lauryl dimethyl hydroxysulfobetaine | 1% |
| (4) | coconut oil fatty acid | 4% |
| (5) | triethanolamine | 4% |
| (6) | dibutylhydroxytoluene | 0.1% |
| (7) | ethanol | 2% |
| (8) | fragrance | 0.5% |
| (9) | water | the balance |

According to the above formulation, the above components (1) to (6) were added to hot water (9) to conduct dissolution. The obtained solution was cooled, followed by the addition of the above components (7) and (8). A transparent body shampoo was prepared. When the skin was washed with this body shampoo, the shampoo was lowly irritant, exhibited a high ability to foam and was excellent in feelings in use.

What is claimed is:

1. A process for the preparation of a phosphoric monoester by reacting an organic hydroxyl compound with a pre-mixed phosphorylating agent consisting essentially of phosphorus pentaoxide and at least one compound selected from the group consisting of water, phosphoric acid and polyphosphoric acid, under such conditions that a) the ratio as defined by formula (I) has a value in the range of from 0.5 to 1.0, and b) the ratio as defined by formula (II) has a value in the range of from 2.8 to 3.2:

$$\frac{\left[\begin{array}{c}\text{Molar amount of phosphorylating}\\\text{agent represented as }P_2O_5\end{array}\right]}{\left[\begin{array}{c}\text{Molar amount of water included}\\\text{in the phosphorylating agent}\\\text{represented as }P_2O_5\cdot n(H_2O)\end{array}\right]} \text{ and} \quad (I)$$

$$\frac{\left[\begin{array}{c}\text{Molar amount of water}\\\text{included in the}\\\text{phosphorylating agent}\\\text{represented as }P_2O_5\cdot n(H_2O)\end{array}\right]+\left[\begin{array}{c}\text{Molar amount}\\\text{of organic}\\\text{hydroxyl}\\\text{compound}\end{array}\right]}{\left[\begin{array}{c}\text{Molar amount of phosphorylating}\\\text{agent represented as }P_2O_5\end{array}\right]}. \quad (II)$$

2. The process according to claim 1, wherein the phosphorylating agent comprises phosphorus pentaoxide and at least one compound selected from the group consisting of water and phosphoric acid.

3. The process according to claim 1, which further comprises a step of hydrolysis of the reaction product.

4. The process according to claim 1, which further comprises a step of deodorization.

5. The process according to claim 1, wherein the organic hydroxyl compound is a linear or branched, saturated or unsaturated alcohol having 6 to 30 carbon atoms, an adduct of a linear or branched, saturated or unsaturated alcohol having 6 to 30 carbon atoms with 1 or more alkylene oxide(s), wherein the alkylene oxide has 2 to 4 carbon atoms and the number of alkylene oxide molecules added is 1 to 100, or an adduct of an alkylphenol, wherein the alkyl moiety has 6 to 20 carbon atoms, with 1 or more alkylene oxide(s), wherein the alkylene oxide has 2 to 4 carbon atoms and the number of alkylene oxide molecules added is 1 to 100.

* * * * *

UNITED STATES PATENT AND TRADEMARK OFFICE
CERTIFICATE OF CORRECTION

| | |
|---|---|
| PATENT NO. | : 6,407,277 B1 |
| APPLICATION NO. | : 08/849211 |
| DATED | : June 18, 2002 |
| INVENTOR(S) | : Matsunaga et al. |

It is certified that error appears in the above-identified patent and that said Letters Patent is hereby corrected as shown below:

On the title page,
Item (*) delete "0" and insert --1229--.

Signed and Sealed this

Fifth Day of December, 2006

JON W. DUDAS
*Director of the United States Patent and Trademark Office*